United States Patent
Osterkamp et al.

(10) Patent No.: US 11,656,617 B1
(45) Date of Patent: May 23, 2023

(54) REMOTE PILOT OF VEHICLE DURING UNSAFE DRIVING CONDITIONS

(71) Applicant: UIPCO, LLC, San Antonio, TX (US)

(72) Inventors: Bryan J. Osterkamp, New Braunfels, TX (US); Gregory Brian Meyer, San Antonio, TX (US); Will Kerns Maney, Jr., San Antonio, TX (US); Ruthie D. Lyle, Durham, NC (US); Deborah Schulz, San Antonio, TX (US); Sean Carl Mitchem, San Antonio, TX (US); Timothy Blair Chalmers, San Antonio, TX (US)

(73) Assignee: United Services Automobile Association (USAA), San Antonio, TX (US)

( * ) Notice: Subject to any disclaimer, the term of this patent is extended or adjusted under 35 U.S.C. 154(b) by 475 days.

(21) Appl. No.: 16/367,431

(22) Filed: Mar. 28, 2019

Related U.S. Application Data

(60) Provisional application No. 62/785,443, filed on Dec. 27, 2018.

(51) Int. Cl.
*G05D 1/00* (2006.01)
*B60W 30/18* (2012.01)
(Continued)

(52) U.S. Cl.
CPC ......... *G05D 1/0055* (2013.01); *A61B 5/0077* (2013.01); *A61B 5/0205* (2013.01); *A61B 5/1128* (2013.01); *A61B 5/18* (2013.01); *A61B 5/4094* (2013.01); *A61B 5/6893* (2013.01); *B60W 30/18* (2013.01); *B60W 40/08* (2013.01);
(Continued)

(58) Field of Classification Search
CPC ............... G05D 1/0055; G05D 1/0011; G05D 2201/0213; A61B 5/0077; A61B 5/0205; A61B 5/1128; A61B 5/18; A61B 5/4094; A61B 5/6893; A61B 5/0531; A61B 5/024; A61B 2562/0204; A61B 2562/0219; B60W 30/18; B60W 40/08; B60W 50/08; B60W 2040/0872; B60W 2040/42;
(Continued)

(56) References Cited

U.S. PATENT DOCUMENTS

2014/0297090 A1* 10/2014 Ichinose ................ G01C 21/28
701/23
2017/0151959 A1* 6/2017 Boesen ................ A61B 5/6803
(Continued)

FOREIGN PATENT DOCUMENTS

DE 102013201168 A1 * 7/2014 ........... G05D 1/0022

OTHER PUBLICATIONS

English translation for reference DE102013201168 (Year: 2014).*

*Primary Examiner* — Rachid Bendidi
(74) *Attorney, Agent, or Firm* — Plumsea Law Group, LLC

(57) ABSTRACT

A system and method for automatically engaging a remote piloting mode in a vehicle is disclosed. The method includes monitoring a driver and switching to the remote piloting mode if an unsafe driving condition is detected. The method can include monitoring biometric data. The method can also include monitoring behavioral data using one or more kinds of vehicle sensors. The system and method ensure vehicles are safely driven even if a driver experiences a health episode that could leave them unable to safely operate the vehicle.

17 Claims, 11 Drawing Sheets

(51) Int. Cl.
  *B60W 40/08* (2012.01)
  *B60W 50/08* (2020.01)
  *A61B 5/18* (2006.01)
  *A61B 5/0205* (2006.01)
  *A61B 5/11* (2006.01)
  *A61B 5/00* (2006.01)
  *A61B 5/024* (2006.01)
  *A61B 5/0531* (2021.01)

(52) U.S. Cl.
  CPC ............ B60W 50/08 (2013.01); G05D 1/0011 (2013.01); *A61B 5/024* (2013.01); *A61B 5/0531* (2013.01); *A61B 2562/0204* (2013.01); *A61B 2562/0219* (2013.01); *B60W 2040/0872* (2013.01); *B60W 2420/42* (2013.01); *B60W 2420/54* (2013.01); *B60W 2520/105* (2013.01); *B60W 2520/28* (2013.01); *B60W 2540/12* (2013.01); *B60W 2540/18* (2013.01); *G05D 2201/0213* (2013.01)

(58) Field of Classification Search
  CPC ....... B60W 2040/54; B60W 2520/105; B60W 2520/28; B60W 2520/12; B60W 2520/18
  See application file for complete search history.

(56) References Cited

U.S. PATENT DOCUMENTS

| | | | |
|---|---|---|---|
| 2017/0274906 A1* | 9/2017 | Hassan | B60K 28/14 |
| 2018/0095457 A1* | 4/2018 | Lee | G08G 1/09623 |
| 2019/0038204 A1* | 2/2019 | Beck | A61B 5/18 |
| 2019/0049267 A1* | 2/2019 | Huang | G06N 20/00 |
| 2019/0147262 A1* | 5/2019 | Kuehnle | G07C 5/008 |
| | | | 340/439 |
| 2019/0265710 A1* | 8/2019 | Kaneko | G08G 1/16 |
| 2019/0339696 A1* | 11/2019 | Mori | G05D 1/0038 |

\* cited by examiner

| AUTONOMY LEVEL | BRIEF DESCRIPTION |
| --- | --- |
| LEVEL 0 | DRIVER CONTROLS EVERYTHING |
| LEVEL 1 | ONE SYSTEM CONTROLLED BY VEHICLE |
| LEVEL 2 | VEHICLE CONTROLS STEERING AND ACCELERATION |
| LEVEL 3 | VEHICLE IN CONTROL, DRIVER REMAINS BACKUP |
| LEVEL 4 | FULLY AUTONOMOUS WITHIN AN OPERATIONAL DESIGN DOMAIN (ODD) |
| LEVEL 5 | FULLY AUTONOMOUS IN ALL DRIVING SCENARIOS |

```
┌─────────────────────────────────┐
│ DETERMINE THAT THERE IS AN      │──1502
│ UNSAFE DRIVING CONDITION        │
└─────────────────────────────────┘
              │
              ▼
┌─────────────────────────────────┐
│ ACTIVATE AUTONOMOUS             │──1504
│ DRIVING MODE                    │
└─────────────────────────────────┘
              │
              ▼
┌─────────────────────────────────┐
│ DETERMINE AUTONOMY LEVEL FOR    │──1506
│ AUTONOMOUS DRIVING MODE         │
└─────────────────────────────────┘
              │
              ▼
┌─────────────────────────────────┐
│ SELECT APPROPRIATE SAFETY       │
│ DRIVING ACTION TO MITIGATE      │──1508
│ UNSAFE DRIVING CONDITION        │
└─────────────────────────────────┘
```

FIG. 15

| AUTONOMY LEVEL | SAFETY DRIVING ACTION |
|---|---|
| LEVEL 1 | DECELERATE VEHICLE SLOWLY TO COME TO SAFE STOP |
| LEVEL 2 | PULL VEHICLE OVER SAFELY ON THE SIDE OF THE ROAD |
| LEVEL 3 | PULL VEHICLE OVER AT NEAREST SAFE DESTINATION |
| LEVEL 4 | CONTINUE ON CURRENT ROUTE WITHIN OPERATIONAL DESIGN DOMAIN TO PREDETERMINED DESTINATION |
| LEVEL 5 | CONTINUE ON CURRENT ROUTE TO PREDETERMINED DESTINATION |

FIG. 16

REMOTE PILOT OF VEHICLE DURING UNSAFE DRIVING CONDITIONS

CROSS-REFERENCE TO RELATED APPLICATIONS

This application claims the benefit of Provisional Patent Application No. 62/785,443 filed Dec. 27, 2018, and titled "Remote Pilot of Vehicle During Unsafe Driving Conditions," which is incorporated by reference herein in its entirety.

TECHNICAL FIELD

The present disclosure generally relates to remotely piloted vehicles, and in particular, to methods for operating remotely piloted vehicles.

BACKGROUND

For drivers with some types of chronic health conditions, driving may be a risky activity. For example, drivers with epilepsy or a history of seizures may be unable to drive because experiencing a seizure while driving could result in incapacitation and an inability to control the vehicle. For such drivers, new autonomous vehicle technologies currently in development may offer hope that they can safely use a vehicle to travel between different locations. However, autonomous vehicle technologies are still in development and fully autonomous vehicles may be years or decades away.

There is a need in the art for a system and method that addresses the shortcomings discussed above.

SUMMARY

In one aspect, a motor vehicle includes a remote piloting mode and a manual driving mode, a remote piloting system for operating the motor vehicle in the remote piloting mode, and a driver monitoring system. The driver monitoring system is configured to detect an unsafe driving condition. The motor vehicle switches from the manual driving mode to the remote piloting mode when the unsafe driving condition is detected.

In another aspect, a method of controlling a motor vehicle that is operable in a remote piloting mode and a manual driving mode includes monitoring a driver while the motor vehicle is operating in the manual driving mode, detecting a critical health event, and switching the motor vehicle from the manual driving mode to the remote piloting mode.

In another aspect, a method of controlling a motor vehicle that is operable in a remote piloting mode where the motor vehicle can be controlled by a remote piloting system, and where the motor vehicle includes at least one vehicle sensor, includes a step of receiving information from the at least one vehicle sensor. The method also includes steps of analyzing the information to detect an unsafe driving behavior, and engaging the remote pilot mode when the unsafe driving behavior is detected.

Other systems, methods, features, and advantages of the disclosure will be, or will become, apparent to one of ordinary skill in the art upon examination of the following figures and detailed description. It is intended that all such additional systems, methods, features, and advantages be included within this description and this summary, be within the scope of the disclosure, and be protected by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like reference numerals designate corresponding parts throughout the different views.

FIG. 15 is a schematic process for selecting an appropriate safety driving action to mitigate unsafe driving conditions, according to an embodiment;

FIG. 16 is a schematic table depicting exemplary safety driving actions for different autonomy levels.

DESCRIPTION OF EMBODIMENTS

The embodiments include systems and methods that allow drivers with chronic health conditions to safely travel in motor vehicles that are less than fully autonomous. These same systems and methods also allow drivers with chronic health conditions to manually drive a vehicle while ensuring that autonomous and/or remote control systems can be engaged at any time that the driver might experience a health episode that could incapacitate them or otherwise result in unsafe driving conditions. In the embodiments shown in FIGS. 1-10, the systems and methods make use of remote piloting technologies in vehicles. In these embodiments, operation of a vehicle can be handed over to a remote piloting system at any point that a potentially unsafe driving condition is detected. In the embodiments shown in FIGS. 11-17, the system and methods make use of autonomous driving technologies in vehicles. In these embodiments, operation of a vehicle can be handed over to an autonomous driving system at any point that a potentially unsafe driving condition is detected.

By activating a remote piloting system when unsafe driving conditions are detected, the systems and methods allow users with chronic health conditions to drive without concern that they may lose control of the vehicle during a health episode (such as a seizure or heart attack). Additionally, the systems and methods reduce the costs associated with remote piloting (for example, costs of paying the remote operator) by limiting remote piloting operations to those times when the driver is experiencing a health episode that could lead to unsafe driving conditions.

Figure 1:
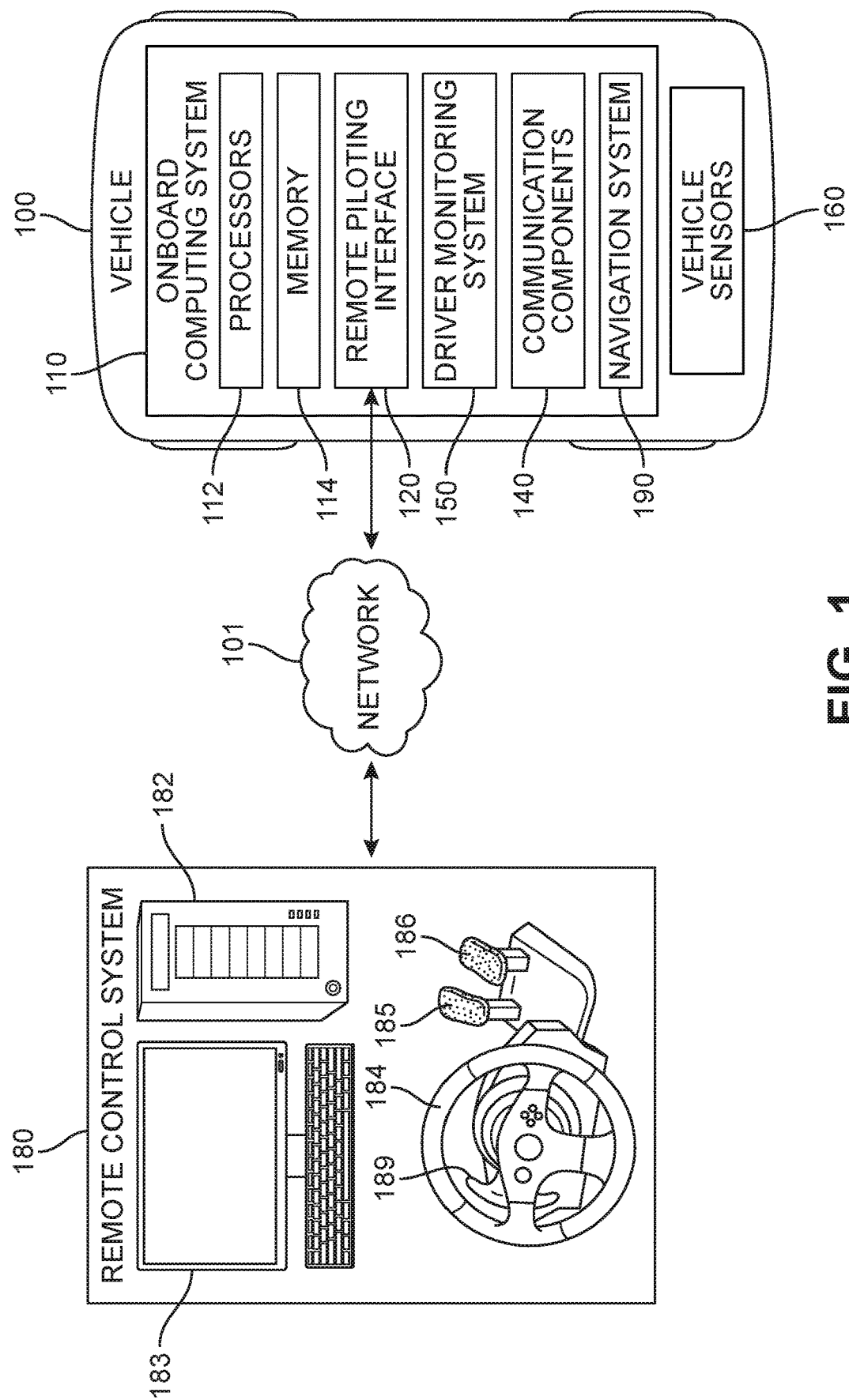
FIG. 1 is a schematic view of an embodiment of a vehicle with a remote piloting interface and a remote control system that together comprise a remote piloting system.

FIG. 1 is a schematic view of a motor vehicle 100, or simply vehicle 100. Vehicle 100 may include an onboard computing system 110. Onboard computing system 110 may comprise a single computing device, or a network of multiple computing devices. Onboard computing system 110 could be associated with one or more electronic control units (ECUs). As seen in FIG. 1, onboard computing system 110 includes one or more processors 112 and memory 114. Memory 114 may comprise a non-transitory computer readable medium. Instructions stored within memory 114 may be executed by the one or more processors 112.

For clarity, some of the vehicle systems of the embodiments are depicted as residing within a single onboard computing system 110. However, it may be appreciated that in some embodiments, one or more of these systems could be separate and may not comprise part of a single computing system. Instead, two or more systems could each comprise their own processors and/or memory, as well as components facilitating communication with other systems.

Vehicle 100 may incorporate features that facilitate remote piloting of the vehicle. The embodiments may utilize any of systems, methods, or other features for remote piloting (or remote operation) that are known in the art. As an example, embodiments may incorporate known methods for streaming real-time data between a remote control system and a remote piloting interface. These may include known methods for compressing video, audio and/or other kinds of data to enable real-time control.

In some embodiments, vehicle 100 may include remote piloting interface 120. Remote piloting interface 120 may communicate with a remote control system 180 over a network 101 (for example, the Internet). Remote control system 180 together with remote piloting interface 120 may comprise parts of a remote piloting system that allows vehicle 100 to be remotely controlled by a human operating remote control system 180.

Figure 2:
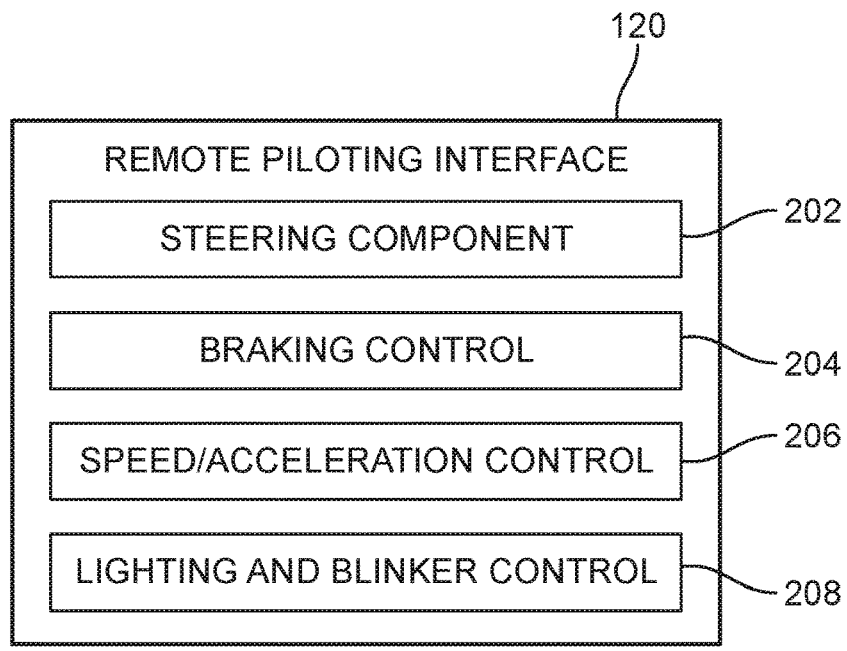
FIG. 2 is a schematic view of some components of a remote piloting interface, according to an embodiment.

Remote piloting interface 120 may include, or communicate with, one or more systems that control various aspects of driving. For example, as seen in FIG. 2, remote piloting interface 120 may include, or communicate with, a steering control system 202, a braking control system 204, a speed/acceleration control system 206, and a lighting and blinker control system 208. These systems may allow an operator of remote control system 180 to steer, brake, accelerate and control lights/blinkers within vehicle 100.

Remote control system 180 may include a computing system 182. Computing system 182 may further include a display 183 for viewing camera feeds and other information useful for remotely piloting a vehicle. Remote control system 180 may also include a steering controller 184, a brake pedal controller 185, an acceleration pedal controller 186 and a lighting/blinker controller 189. The outputs of these control components may be fed into computing system 182 and then sent to vehicle 100 over network 101. Thus, for example, when an operator presses brake pedal controller 185, a braking command is sent to computing system 182, then to remote piloting interface 120. Remote piloting interface 120 then instructs braking control system 204 to actuate the brakes on vehicle 100.

A remote control system can be operated by any suitably trained user. In some embodiments, a remote control system may be operated by employees of a third party service. This service could be available at any time, for example, to take control of a vehicle when such an action is necessary. Alternatively, a remote control system could be operated by a family member, friend, or other party who is available and able to remotely pilot a vehicle. In the case where the vehicle is remotely controlled by a friend or family member, for example, the remote control system could be provided as virtual controls within a software application, such as a mobile application.

Figure 3:
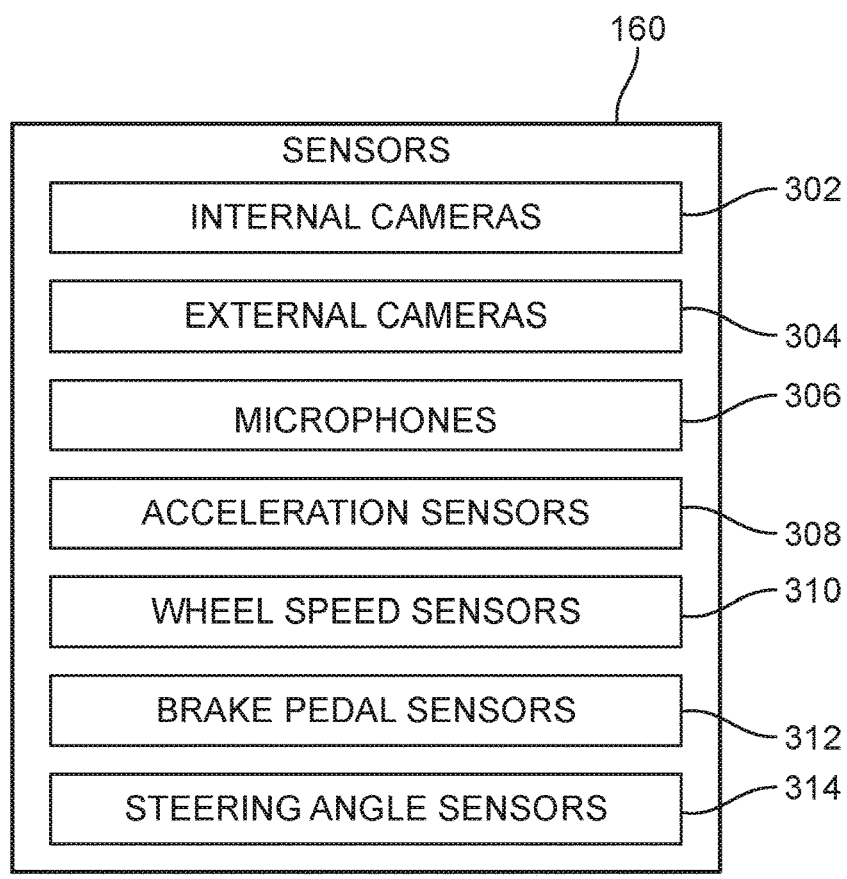
FIG. 3 is a schematic view of a set of vehicle sensors, according to an embodiment.

Sensory information from vehicle 100 can be passed to remote control system 180 to simulate the driving environment of vehicle 100. Vehicle 100 may include vehicle sensors 160. As seen in FIG. 3, vehicle sensors 160 can include one or more internal cameras 302, external cameras 304, and microphones 306. Using internal and external cameras, as well as microphones, an operator of remote control system 180 may be able to see and hear what a driver within vehicle 100 could see and hear. This allows the operator to make decisions about steering, vehicle speed, braking, turning on/off headlights, using blinkers for turning as well as other kinds of driving decisions.

Additionally, other kinds of sensed information could be sent to remote control system 180. This includes information from acceleration sensors 308 (for example, an acceleration pedal sensor), wheel speed sensors 310, brake pedal sensors 312, and steering angle sensors 314. Although not shown, some embodiments could also include LIDAR and/or RADAR based sensors for sensing objects (such as other cars) in the vehicle's environment. Information from one or more of these sensors could be used to provide feedback to remote control system 180, ensuring that driving commands (for example, a braking command) are being performed as desired by the corresponding vehicle control system (for example, the braking control system).

Vehicle 100 may also include one or more communication components 140. Communication components 140 may include cellular network components for communicating over cellular networks, Wi-Fi components for communicating over Wi-Fi networks, and other communication components. Using one or more communication components 140, vehicle 100 may communicate with remote control system 180.

Vehicle 100 may also include a navigation system 190. In some cases, navigation system 190 includes a GPS receiver that can receive GPS information. In other cases, navigation system 190 can include other receivers capable of receiving global or local positioning information. Additionally, navigation system 190 may comprise maps and/or information from other kinds of geographic information systems (GIS) that can be used to generate navigation routes for a driver.

Vehicle 100 may also include an onboard diagnostics (OBD) system, which is not shown for clarity. An OBD system may track and process various vehicle sensor information. In some cases, one or more systems of vehicle 100 could retrieve sensory data from the OBD system rather than directly from the sensors themselves.

Figure 4:
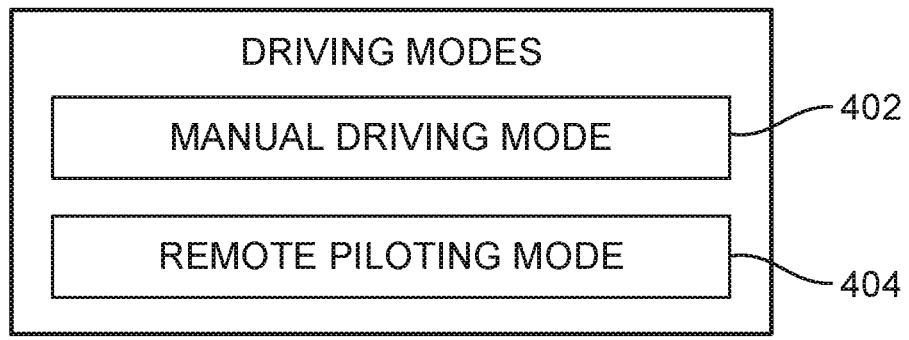
FIG. 4 is a schematic view of two possible driving modes for the vehicle of FIG. 1, according to an embodiment.

As seen in the schematic view of FIG. 4, vehicle 100 may be operated in two different modes. These include a manual driving mode 402 and a remote piloting mode 404. Manual driving mode 402 corresponds to a mode in which a driver physically present in vehicle 100 operates the vehicle. By contrast, remote piloting mode 404 corresponds to a mode in which a remote operator not located within vehicle 100 operates the vehicle using a remote control system (for example, remote control system 180).

In some embodiments, a driver may manually switch between a manual driving mode and a remote piloting mode. This may be useful for drivers who occasionally cannot drive due to physical limitations. It may also be useful when a driver becomes inebriated and needs to get home without driving the vehicle. Also, the remote piloting mode could be used when a driver simply prefers not to drive. In other embodiments, a vehicle may include provisions for automatically switching from a manual driving mode to a remote piloting mode. In some embodiments, a vehicle includes systems that may detect when a driver is unable to drive safely and may automatically enable the remote piloting mode in response.

As seen in FIG. 1, vehicle 100 may include a driver monitoring system 150. Driver monitoring system 150 may be configured to monitor drivers to detect unsafe driving conditions. Unsafe driving conditions may correspond to conditions where it is unsafe to let a driver continue operating the vehicle and thus the system may communicate with remote piloting interface 120 to enable the remote piloting mode.

A driver monitoring system may detect when a driver is possibly experiencing a critical health event that might increase driving risks. Examples of critical health events include seizures, strokes, and heart attacks. Additional examples of critical health events that may increase driving risks include narcoleptic conditions, such as cataplexy and sleep paralysis. During these critical health events a driver may become incapacitated and unable to control the vehicle safely.

In some embodiments, a driver monitoring system could detect critical health events by monitoring the real-time health of a driver. This may include monitoring various kinds of biometric data for the driver. Examples of biometric data include, but are not limited to: heart rate, breathing rate, electrodermal activity, skin temperature, and muscle contractions. For example, an extremely high or erratic heart rate could be indicative of a heart attack. In addition, abnormal changes in heart rate, electrodermal activity, skin temperature and/or muscle contractions could be indicative of a seizure.

In some embodiments, a driver monitoring system could detect critical health events by monitoring the external behavior of a driver. Examples of external behaviors include, but are not limited to: body motions and speech patterns. For example, if a driver's head is slumped down, or if their speech is slurred, it may be indicative of a critical health event that has caused them to lose control of the vehicle. Likewise, if a driver has erratically turned the steering wheel and/or pressed on the accelerator, it may be indicative of a critical health event that has caused them to lose control of the vehicle.

Figure 5:
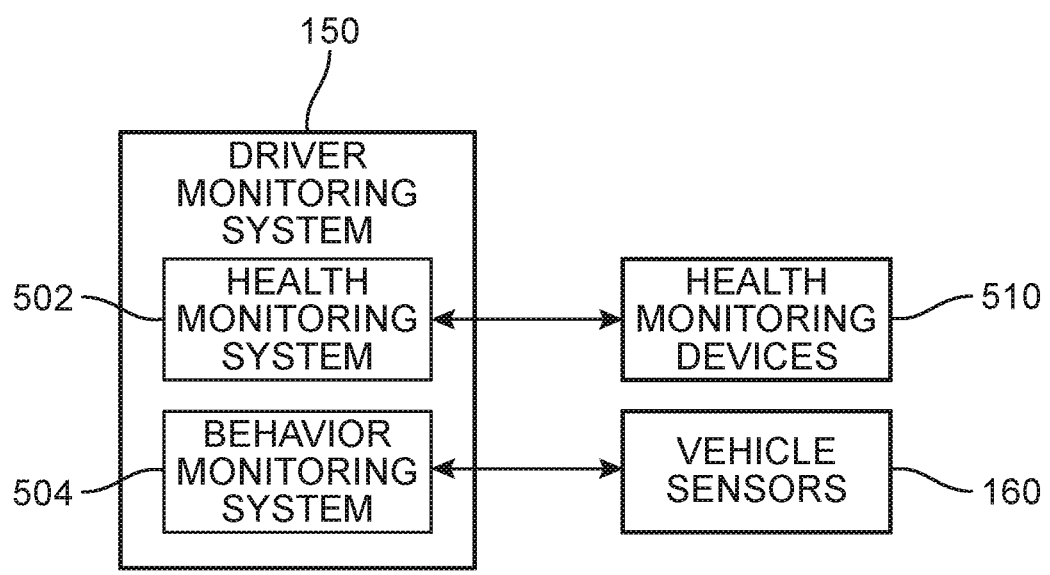
FIG. 5 is a schematic view of a driver monitoring system, according to an embodiment.

Referring now to FIG. 5, driver monitoring system 150 can further include a health monitoring system 502 and a behavior monitoring system 504. Health monitoring system 502 may include a system that monitor a driver's health in real time, and detects when a critical health event occurs that might result in unsafe driving conditions. To monitor the real-time health of a driver, health monitoring system 502 may communicate with one or more health monitoring devices 510, which are described in further detail below.

Behavior monitoring system 504 may include a system that monitors a driver's outward behavior. A driver's outward behavior could be sensed using one or more vehicle sensors 160. For example, cameras and/or microphones could be used to detect when a driver is unresponsive or otherwise moving (or speaking) in an erratic manner. In this case, data from internal cameras 302 and microphones 306 could be used. In addition, real-time driving data could be used to determine if a driver is steering, accelerating and/or braking erratically. In this case, information from acceleration sensors 308, steering angle sensors 314, wheel speed sensors 310 and/or brake pedal sensors 312 could be used.

If either health monitoring system 502 or behavior monitoring system 504 detect an unsafe driving condition, driver monitoring system 150 could communicate with remote piloting interface 120 to enable the remote piloting mode and turn off the manual driving mode.

Figure 6:
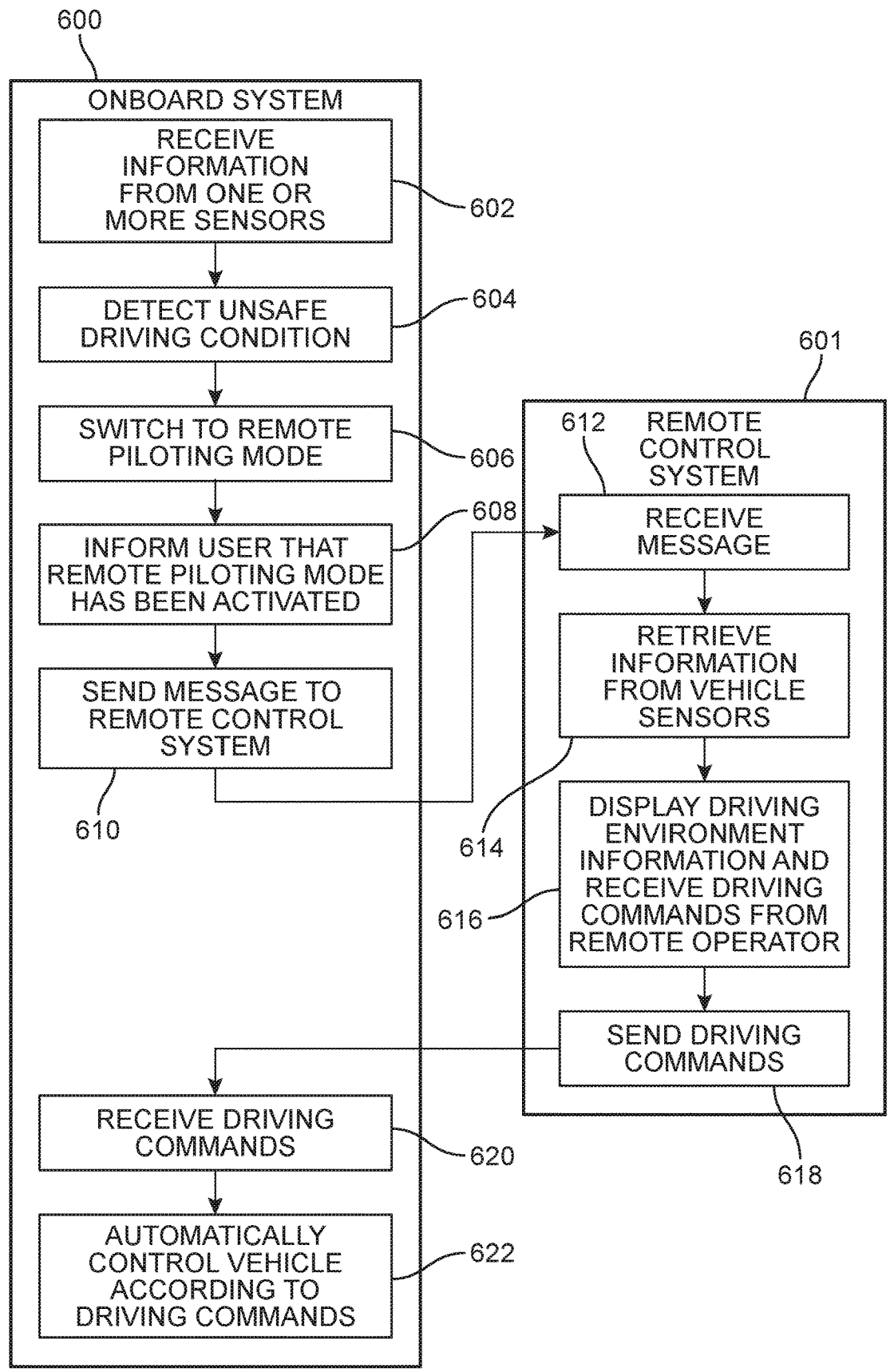
FIG. 6 is a schematic process for detecting unsafe driving conditions and switching to a remote piloting mode, according to an embodiment.

FIG. 6 is a schematic view of a process for detecting unsafe driving conditions and enabling remote piloting in response. In the exemplary embodiment, some steps may be performed by an onboard system 600 and other steps may be performed by a remote control system 601. Onboard system 600 may comprise onboard computing system and/or any combination of individual vehicle systems. In the exemplary embodiment, onboard system 600 is comprised of remote piloting interface 120, driver monitoring system 150 and communication components 140. Onboard system 600 further receives information from various onboard vehicle sensors 160. Onboard system 600 may also receive information from one or more health monitoring devices 510, which may be portable electronic devices as described in further detail below.

In a first step 602, onboard system 600 receives information from one or more sensors. This sensory information could include biometric data (such as heart rate data), environmental data (such as video/image data and/or audio data), and/or vehicle systems data (such as vehicle speed, steering angle, etc.). Based on this information, onboard system 600 may detect an unsafe driving condition in step 604. Specifically, driver monitoring system 150 monitors the sensory information and detects unsafe driving conditions.

In step 606, onboard system 600 switches the vehicle to a remote piloting mode. In some cases, this occurs when driver monitoring system 150 detects an unsafe driving condition and instructs remote piloting interface 120 to engage the remote piloting mode. In some cases, during an optional step 608, onboard system 600 may inform the user/driver that the remote piloting mode has been activated. This could include sending a message to an onboard display or other device. Alternatively, this could include making an audible announcement. Informing the driver of the change in operating mode is useful if a driver has lost control of the vehicle but is still conscious and therefore may be relieved to know that the vehicle will continue to be operated remotely.

In step 610, onboard system 600 sends a message to remote control system 601, which is received by remote control system 601 at step 612. Next, remote control system 601 may retrieve information from vehicle sensors 160 in step 614. This may include video information, audio information as well as information from various vehicle systems (such as the current vehicle speed and the current steering angle).

Next, in step 616, remote control system 601 may display the driving environment information for the remote operator. During this step remote control system 601 may also receive driving commands from the remote operator. For example, remote control system 601 may receive steering commands through steering controller 184, a brake pedal controller 185, and an acceleration pedal controller 186 (see FIG. 1).

Next, in step 618, remote control system 601 may send driving commands to onboard system 600. After receiving driving commands in step 618, onboard system 600 may proceed to step 620. In step 620, onboard system 600 automatically controls the vehicle according to the received driving commands.

It may be appreciated that once the remote piloting mode is activated information may be continuously passed back and forth between onboard system 600 and remote control system 601. This allows the remote control system 180 to receive real-time driving information and respond with new driving commands (for example, new steering commands and new acceleration commands) that are then implemented by onboard system 600. This cycle may continue until the remote piloting mode is deactivated.

Figure 7:
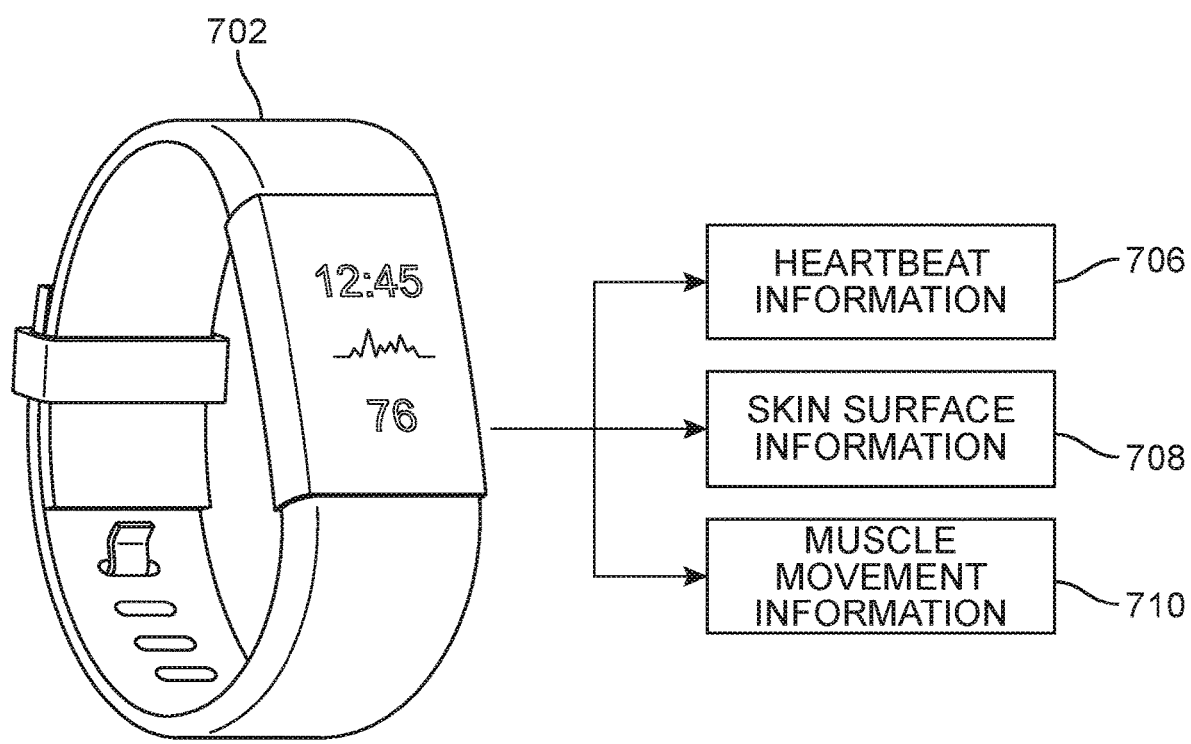
FIG. 7 is a schematic view of an embodiment of a health monitoring device.

FIG. 7 depicts a schematic view of a health monitoring device 702. In this case, health monitoring device 702 takes the form of a smart watch with built in biometric sensors. Health monitoring device 702 includes one or more sensors that can be used for detecting heartbeat (or heart rate) information 706, skin surface information 708 (such as sweat levels and temperature) and/or muscle movement information 710. As an example, some smartwatches are able to detect potential seizures by analyzing unusual patterns in movement and physiological activity. In some cases, these smartwatches include electrodermal activity (EDA) sensors, gyroscopes, accelerometers and peripheral temperature sensors.

Figure 8:
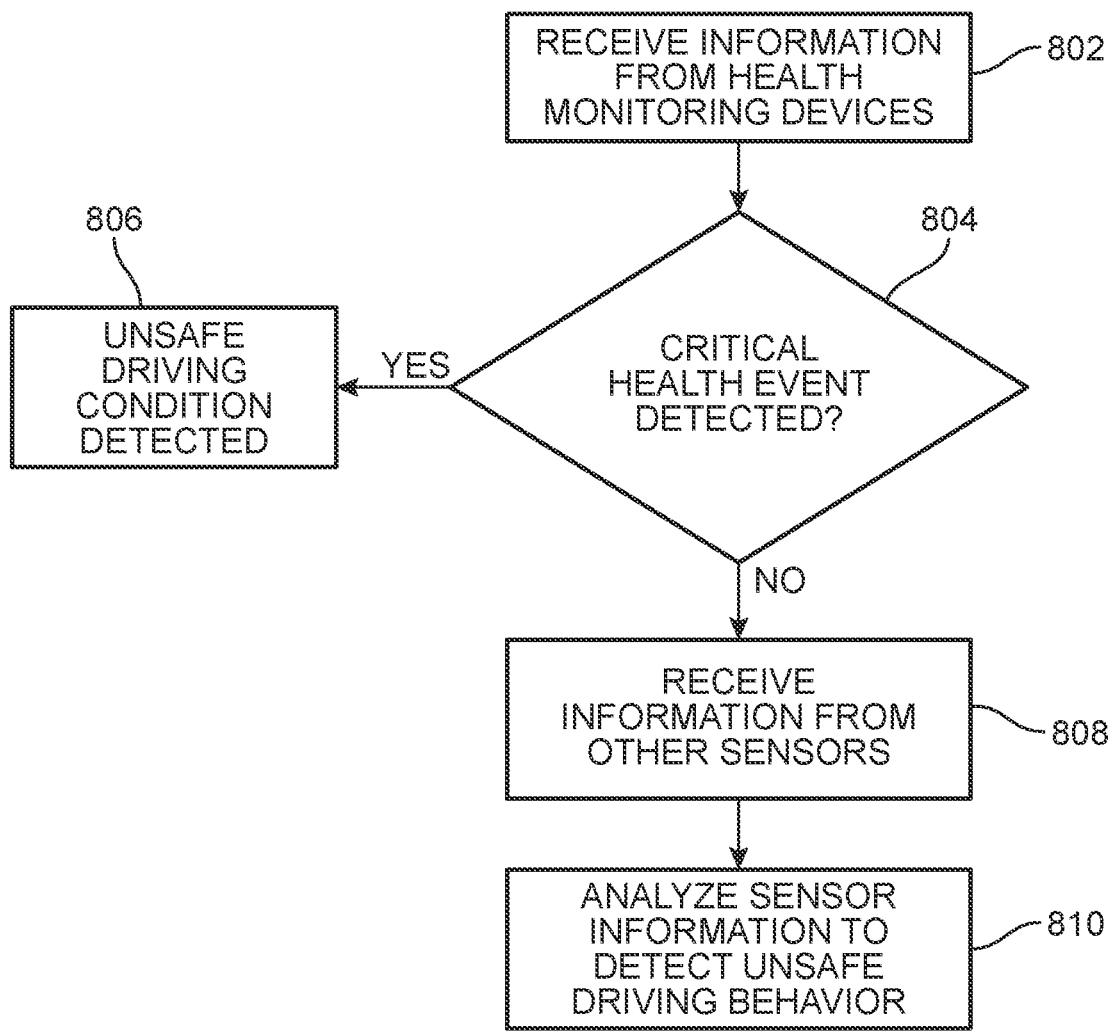
FIG. 8 is a schematic process for detecting unsafe driving conditions, according to an embodiment.

FIG. 8 is a schematic view of a process for detecting unsafe driving conditions. In some embodiments, some or all of the following steps could be performed by a driver monitoring system, such as driver monitoring system 150. In step 802, driver monitoring system 150 may receive information from one or more health monitoring devices (such as health monitoring device 702). Next, in step 804, driver monitoring system 150 may determine if a critical health event has been detected. Examples of critical health events that could result in unsafe driving conditions include, but are not limited to: heart attacks, strokes, and seizures.

If a critical health event has been detected, driver monitoring system 150 may proceed to step 806 where driver monitoring system 150 determines that an unsafe driving condition (in particular, a critical health event) has been detected. That is, if the system detects a possible critical health event, then it is assumed that this may result in unsafe driving conditions (such as erratic movements, or incapacitation). If a critical health event has not been detected in step 804, driver monitoring system 150 may proceed to step 808. At step 808, driver monitoring system 150 may receive information from other sensors (such as vehicle sensors 160). In step 810, driving monitoring system 150 may analyze the sensor information from step 808 to detect unsafe driving behavior. Thus, the above process can detect unsafe driving conditions by examining real-time biometric data and/or by examining external behaviors of the driver.

Figure 9:
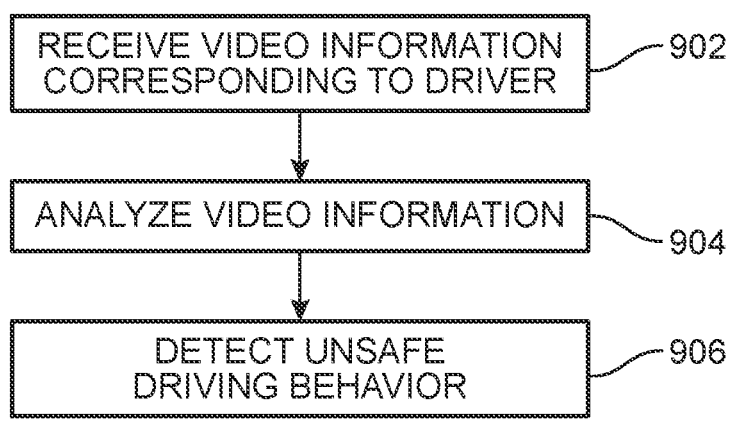
FIG. 9 is a schematic process for detecting unsafe driving behavior, according to an embodiment.

FIG. 9 is a schematic view of an embodiment of a process for analyzing video information to detect unsafe driving behavior. In some embodiments, one or more of the following steps could be performed by behavior monitoring system 504. Starting at step 902, behavior monitoring system 504 may receive video information corresponding to the driver. The video information could be received from one or more internal cameras 302 (see FIG. 3) that are positioned to capture video images of the driver. Next, in step 904, the video information could be analyzed as discussed in further detail below. In step 906, behavior monitoring system 150 may detect an unsafe driving behavior. Although the exemplary process depicted in FIG. 9 includes the use of video information, in other embodiments audio information could be used. In that case, rather than detecting problematic movements, the system could detect problematic speech patterns or other sounds.

Figure 10:
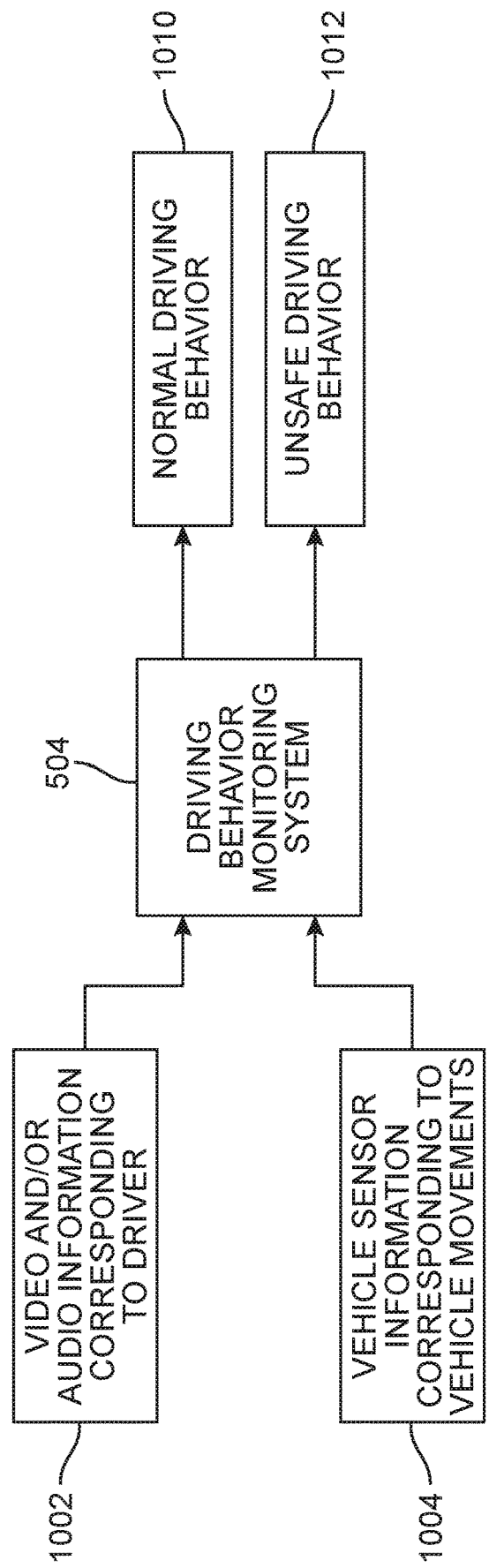
FIG. 10 is a schematic view of a driving behavior monitoring system, according to an embodiment.

FIG. 10 is a schematic view of driving behavior monitoring system 504, including inputs and outputs. As inputs, driving behavior monitoring system may receive video and/or audio information 1002 corresponding to the driver. Additionally, vehicle sensor information corresponding to vehicle movements 1004 may also be received as input. These inputs may then be analyzed to categorize any current behavior as normal driving behavior 1010 or unsafe driving behavior 1012.

Sensory information, including video information, audio information and other suitable sensory information, could be analyzed using any known machine learning methods. In some embodiments, a machine learning model could be trained to identify unsafe driving behaviors, including unresponsive behaviors associated with health conditions like heart attacks and seizures.

Additionally, biometric information, including heart rate information, skin temperature information, electrodermal activity information, body motion information or other suitable kinds of biometric information could be analyzed using any known machine learning methods. In some embodiments, a machine learning model could be trained to identify critical health events, including heart attacks and seizures.

The principles of embodiments described above and shown in FIGS. 1-10 can also be applied to autonomous vehicles. That is, in autonomous vehicles that can operate between a manual driving mode and an autonomous driving mode, the exemplary systems and methods described above can be used to automatically engage the autonomous driving mode when an unsafe driving condition is detected.

By activating an autonomous driving mode when unsafe driving conditions are detected, the systems and methods allow users with chronic health conditions to drive without concern that they may lose control of the vehicle during a health episode. Additionally, the systems and methods make it possible for users with chronic health conditions to make use of vehicles that have partial autonomy, by allowing users to control the vehicle in driving scenarios that are not manageable by the autonomous system and limiting autonomous driving to emergency situations.

Figure 11:
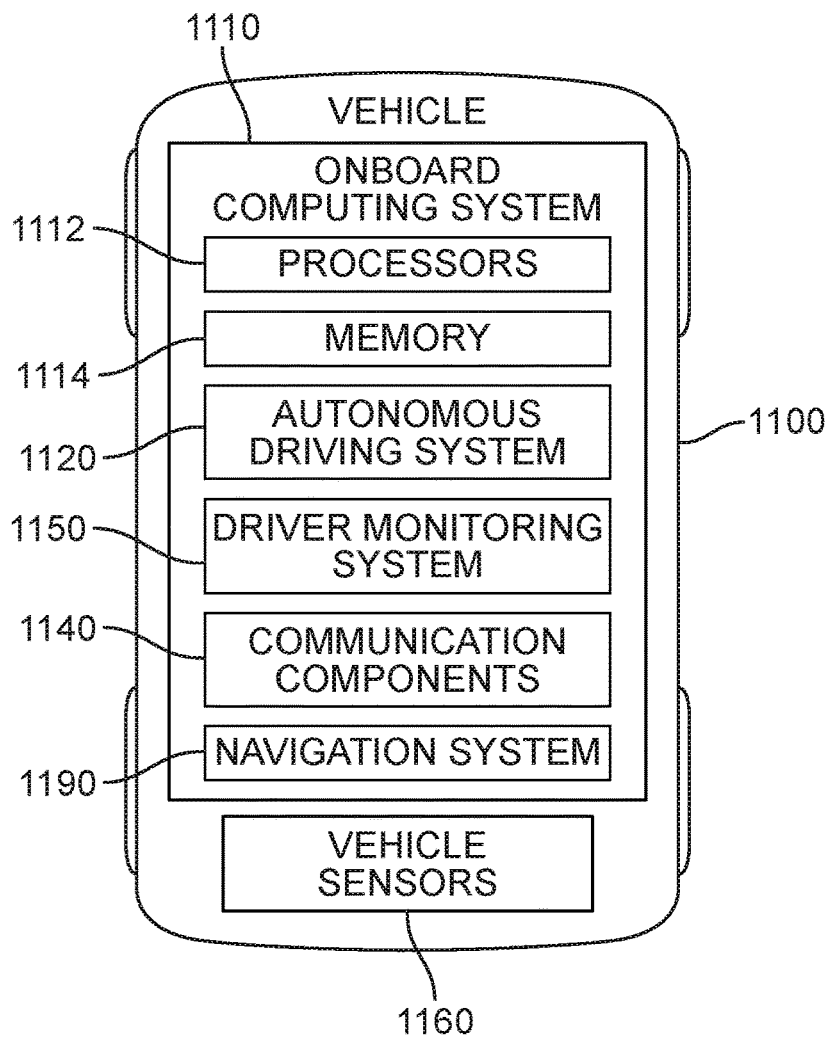
FIG. 11 is a schematic view of an embodiment of an autonomous vehicle.

FIG. 11 is a schematic view of a vehicle 1100. Vehicle 1100 may include an onboard computing system 1110. Onboard computing system 1110 may comprise a single computing device, or a network of multiple computing devices. Onboard computing system 1110 could be associated with one or more electronic control units (ECUs). As seen in FIG. 11, onboard computing system 1110 includes one or more processors 1112 and memory 1114. Memory 1114 may comprise a non-transitory computer readable medium. Instructions stored within memory 1114 may be executed by the one or more processors 1112.

Vehicle 1100 may incorporate features that facilitate autonomous driving of the vehicle. In some embodiments, vehicle 1100 may include autonomous driving system 1120. Autonomous driving system 1120 may include systems, components and methods known in the art for controlling vehicles autonomously. Autonomous driving system 1120 may include both hardware, including the sensors described above, and software for controlling vehicles autonomously. For example, autonomous driving system 1120 may include one or more known machine learning algorithms that identify and react to objects in video images for purposes of controlling vehicles and avoiding collisions.

Autonomous driving system 1120 may include, or communicate with, one or more systems that control various aspects of driving. In some embodiments, autonomous driving system 1120 includes, or communicates with, a steering control system 202, a braking control system 204, a speed/acceleration control system 206, and a lighting and blinker control system 208, which were introduced above and shown in FIG. 2. These systems may allow an autonomous driving system to steer, brake, accelerate and control lights/blinkers within vehicle 1100. In addition, other suitable control systems could also be used, including any other control systems known in the art for use in autonomous vehicles.

Sensory information from vehicle 1100 can be passed to autonomous driving system 1120 using one or more vehicle sensors 1160. Sensory information can be received by various kinds of sensors, including any of the sensors described above and shown in FIG. 3, as well as LIDAR and/or RADAR based sensors. Using this sensory information allows an autonomous driving system to make decisions about steering, vehicle speed, braking, turning on/off headlights, and using blinkers for turning.

Vehicle 1100 may also include various communication components 1140. These may include any of the communication components 140 described above for vehicle 100. Additionally, vehicle 1100 may also include a navigation system 1190, which may be similar to navigation system 190 described above.

Figure 12:
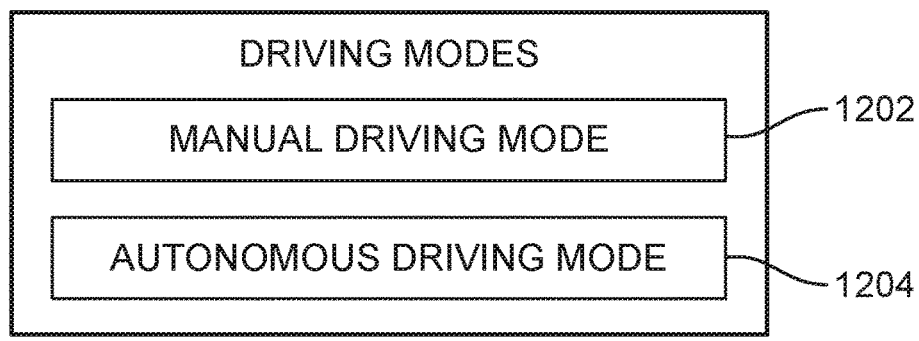
FIG. 12 is a schematic view of two possible driving modes for the vehicle of FIG. 11.

As seen in the schematic view of FIG. 12, vehicle 1100 may be operated in two different modes. These include a manual driving mode 1202 and an autonomous driving mode 1204. Manual driving mode 1202 corresponds to a mode in which a driver physically present in vehicle 1100 operates the vehicle. By contrast, autonomous driving mode 1204 corresponds to a mode in which the autonomous driving system has control over one or more vehicle systems (for example, a steering system and/or an acceleration system).

As autonomous driving systems are phased into the consumer market on over time, some drivers may still prefer to manually drive their vehicles at times. Therefore, drivers may have the option to switch between a manual driving mode and an autonomous driving mode. In some embodiments, a vehicle may include provisions for automatically switching from a manual driving mode to an autonomous driving mode. In some embodiments, a vehicle includes systems that may detect when a driver is unable to drive safely and may automatically enable the autonomous driving mode in response.

As seen in FIG. 11, vehicle 1100 may include a driver monitoring system 1150. Driver monitoring system 1150 may be configured to monitor drivers to detect unsafe driving conditions. Unsafe driving conditions may correspond to conditions where it is unsafe to let a driver continue operating the vehicle and thus the system may communicate with autonomous driving system 1120 to enable the autonomous driving mode.

Driver monitoring system 1150 may be similar in some, or all, respects to driver monitoring system 150 described above and shown in FIG. 1. It may therefore be appreciated that some or all of the systems and methods described above and depicted in FIGS. 5-10 could be used in association with vehicle 1100.

Figures 13, 14:
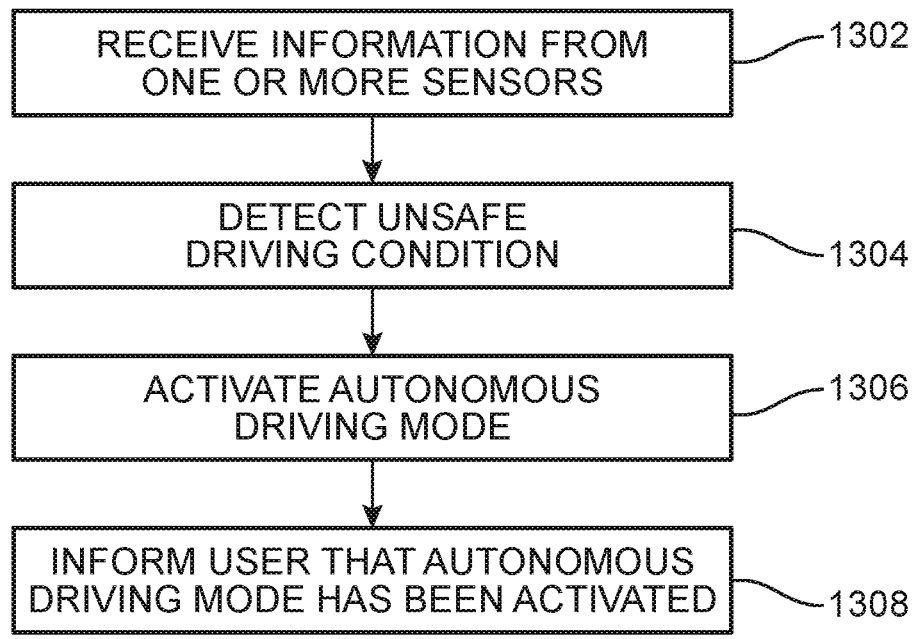
FIG. 13 is a schematic view of a process for engaging an autonomous driving mode in response to detecting unsafe driving conditions, according to an embodiment.
FIG. 14 is a schematic table of various autonomy levels for autonomous vehicles, according to an embodiment.

FIG. 13 is a schematic view of a process for automatically activating the autonomous driving mode 1204 in response to detecting an unsafe driving condition. In the exemplary embodiment, some steps may be performed by an onboard system. The onboard system may comprise an onboard computing system and/or any combination of individual vehicle systems. In the exemplary embodiment, the onboard system is comprised of at least autonomous driving system 1120 and driver monitoring system 1150. The onboard system further receives information from various onboard vehicle sensors 1160. The onboard system may also receive information from one or more health monitoring devices (for example, health monitoring device 702 in FIG. 7).

In a first step 1302, the onboard system receives information from one or more sensors. This sensory information could include biometric data (such as heart rate data and/or skin temperature data), environmental data (such as video/image data and/or audio data), and/or vehicle systems data (such as vehicle speed and/or steering angle data). Based on this information, the onboard system may detect an unsafe driving condition in step 1304. Specifically, driver monitoring system 1150 monitors the sensory information, analyzes the information, and detects unsafe driving conditions.

In step 1306, the onboard system switches the vehicle to an autonomous driving mode. In some cases, this occurs when driver monitoring system 1150 detects an unsafe driving condition and instructs autonomous driving system 1120 to engage the autonomous driving mode. In some cases, during an optional step 1308, the onboard system may inform the user/driver that the autonomous driving mode has been activated. Informing the driver of the change in operating mode is useful if a driver has lost control of the vehicle but is still conscious and therefore may be relieved to know that the vehicle will continue to be operated autonomously.

In different embodiments, autonomous driving system 1120 may be partly autonomous or fully autonomous. As shown in FIG. 14, an autonomous vehicle (or a vehicle operating in an autonomous driving mode) may be configured to operate according to one or more "autonomy levels". The exemplary autonomy levels described in the table of FIG. 14 are levels devised by the U.S. Department of Transportation's National Highway Traffic Safety Administration (NHTSA).

Referring to FIG. 14, Level 0 corresponds to lack of any autonomy. At this level the driver controls everything. Level 1 autonomy corresponds to a situation where at least one system is controlled by the vehicle. This could include a situation where the vehicle handles steering, or acceleration, but the driver performs all other driving functions. Level 2 autonomy corresponds to a situation where the vehicle controls steering and acceleration, but the driver is responsible for other functionality. As an example, a vehicle using both lane keep assistance and cruise control simultaneously may be operating at level 2 autonomy, at least within a narrow operating domain. Level 3 autonomy corresponds to a situation where the vehicle is in control of all safety critical driving functions, but the driver remains available to provide backup if the autonomous system fails or needs assistance.

Level 4 autonomy corresponds to a situation where the vehicle is fully autonomous within a particular operational design domain (ODD). Here, the ODD may refer to a specific set of driving scenarios, such as driving on a highway, driving on city streets, etc. However, level 4 autonomous vehicles may not be capable of operating fully autonomously outside their ODD. For example, a vehicle that can operate autonomously on a highway but cannot operate on a dirt road may have level 4 autonomy. Level 5 autonomy corresponds to a vehicle that is fully autonomous in all driving scenarios.

With respect to the present embodiments, manual driving mode 1202 may correspond to operating the vehicle at level 0 autonomy. By contrast, the autonomous driving mode 1204 could be associated with one or more levels of autonomy. In some cases, vehicle 1100 may operate at level 1 autonomy in the autonomous driving mode 1204. In other cases, vehicle 1100 may operate at level 2 autonomy in the autonomous driving mode 1204. In still other cases, vehicle 1100 may operate at level 3 autonomy in the autonomous driving mode 1204. In still other cases, vehicle 100 may operate at level 4 autonomy in the autonomous driving mode 1204. In still other cases, vehicle 1100 may operate at level 5 autonomy in the autonomous driving mode 1204.

The level of autonomy may determine the available options that an autonomous vehicle can take to mitigate the current unsafe driving conditions. This process is depicted schematically in FIG. 15. Starting at step 1502, an onboard system may determine that there is an unsafe driving condition using one or more of the processes described above. Next, in step 1504, the onboard system may activate the autonomous driving mode.

In step 1506, the onboard system may determine an autonomy level for the autonomous driving mode. For example, the onboard system may determine if the vehicle has level 1, level 2, level 3, level 4 or level 5 autonomy, according to the classification described above and shown in FIG. 14. Based on the autonomy level, the onboard system may select an appropriate safety driving action to mitigate the unsafe driving condition.

FIG. 16 is a schematic view of a table of sample safety driving actions that an autonomous vehicle can perform to mitigate unsafe driving conditions. It may be appreciated that this table only lists exemplary actions, and many other actions are possible. Referring to FIG. 16, if the system has level 1 autonomy, the autonomous driving system may take actions to decelerate the vehicle slowly and come to a safe stop, so long as such an action is safe in the driving context. This may be safe for a vehicle operating on a small neighborhood road, but not for a vehicle traveling on a highway.

If the system has level 2 autonomy, the autonomous driving system may take actions to pull the vehicle over safely on the side of the road. This may be possible since level 2 autonomy provides automated control over both steering and acceleration/deceleration.

If the system has level 3 autonomy, meaning all safety critical systems are autonomous but a user is still required to be available to take over, the autonomous driving system could wait to pull the vehicle over at a nearest safe destination. For example, pulling over at a rest stop may be much safer for the driver than pulling over onto a narrow shoulder on a highway.

If the system has level 4 autonomy, the autonomous vehicle system may continue on any current route within the operational design domain to a predetermined destination. Likewise, if the system has level 5 autonomy, the autonomous vehicle system may continue on the current route to the predetermined destination without regard for an operational design domain.

Figure 17:
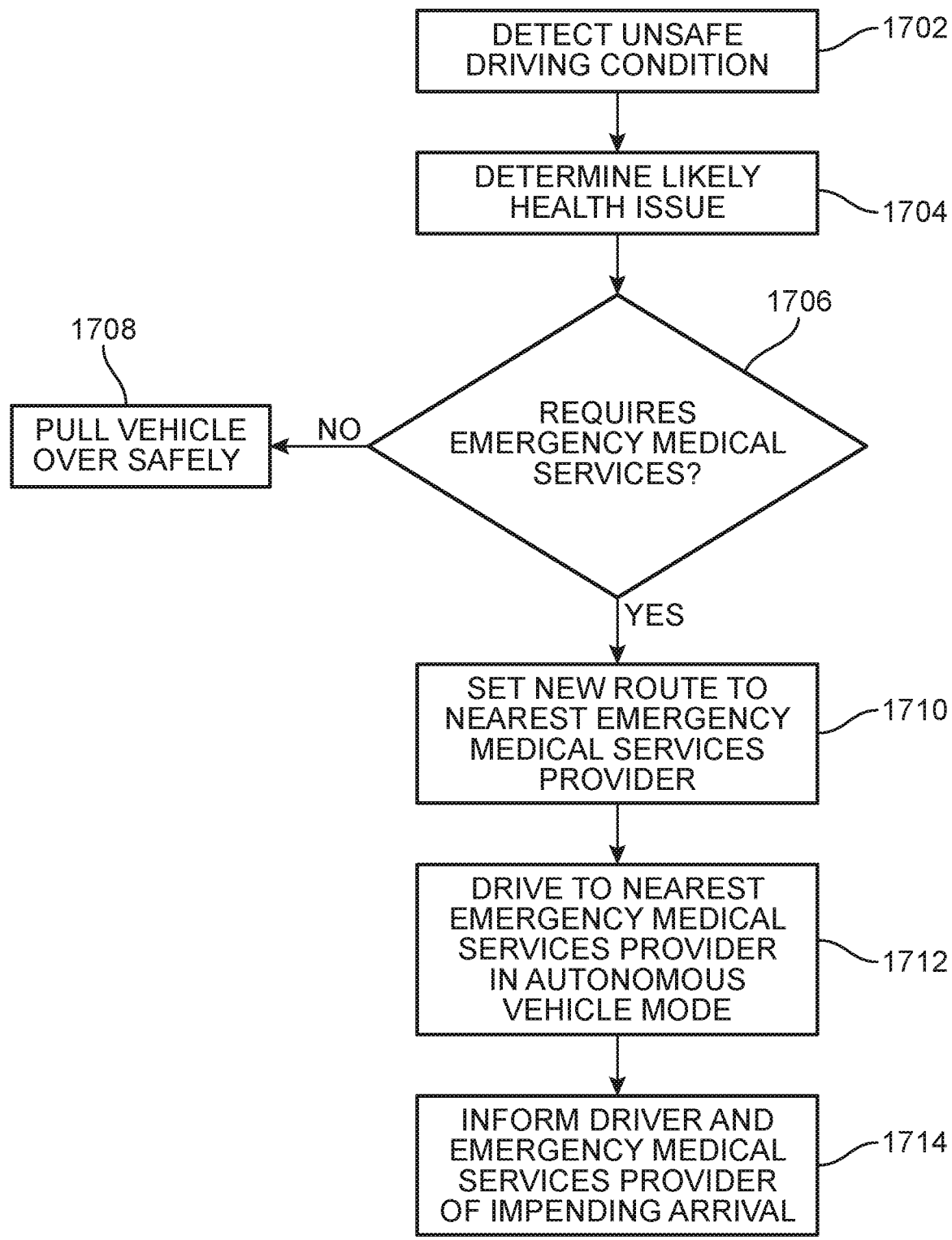
FIG. 17 is a schematic process for automatically re-routing a vehicle to an emergency medical services provider, according to an embodiment.

FIG. 17 is a schematic view of a process for driving an occupant to a nearest medical services provider when a health issue requiring medical services is detected. As user herein, an emergency medical services provider could be a hospital, clinic, doctor's office or any other suitable provider.

In a first step 1702, an onboard system may detect an unsafe driving condition using any of the methods described above. Next, in step 1704, the onboard system may determine any likely health issues that may correspond with the detected unsafe driving conditions. For example, using a health monitoring device, the onboard system may detect signs of a heart attack. Based on this information, the onboard system may determine if the likely health issue requires emergency medical services in step 1706. For example, a heart attack may require emergency medical services, while some seizure patients may not require emergency care following a mild seizure.

If emergency medical services are not needed, the onboard system may take the appropriate autonomous actions to pull the vehicle over safely in step 1708. If emergency medical services are needed, the onboard system may set a new route to a nearest emergency medical services provider in step 1710. In some embodiments, the nearest emergency medical services provider could be determined by navigation system 1190.

Next, in step 1712, the onboard system may drive to the nearest emergency medical services provider using its autonomous driving mode. In some embodiments, the onboard system may further inform a driver of the current plan to drive to the emergency medical services provider in step 1714. Additionally, in some embodiments, the onboard system could also send a message to the emergency medical services provider of the occupant's impending arrival, and possible the need for assistance (such as a wheel chair).

Alternatively, in some embodiments, if a system determines that a likely health issue requires emergency medical services, the system could pull over and contact a 911 operator to request help at the present location.

In deciding where to take a user undergoing a critical health event, a system could consider additional factors beyond proximity to an emergency medical services provider. For example, a system with access to a user's insurance information could be configured to take a user to the nearest emergency services provider that also takes the user's health insurance. Alternatively, the system could compare costs at different emergency service providers, and/or quality of care as determined by online reviews or other retrieved rating information.

Though the illustrated embodiments depict examples where a system automatically detects when it may be necessary to switch from manual control of a vehicle to either remote piloting or autonomous control, in other embodiments a user of the vehicle could take steps to engage either remote piloting or autonomous control manually. In some embodiments, voice commands could be used to engage remote piloting or autonomous control. In one embodiment, voice commands could be detected by microphones 306 (see FIG. 3). Software running on the onboard computing system could process these spoken commands and take action to change the driving mode. For example, a keyword could be used to tell a system to automatically engage remote piloting or autonomous control, depending on what type of system is available in the vehicle. Using keyword commands may allow a driver to engage remote piloting or autonomous driving prior to having a critical health event. For example, some people who suffer from seizures or migraines often have a sense that such a health event is going to occur soon. By automatically changing the driving mode of the vehicle using keywords ahead of (or at the onset of) a critical health event, remote piloting or autonomous driving can be used to get a user to a safe situation as soon as possible.

The embodiments make use of one or more motor vehicles. As used herein, the term "motor vehicle," or simply vehicle, refers to any kind of car, van, truck, motorcycle, or similar motorized vehicle. A motor vehicle can be powered using an internal combustion engine, an electric motor, a hybrid of an internal combustion engine and an electric motor, as well as any other suitable power source. A motor vehicle may further include wheels that are powered by the engine or motor and components for controlling the vehicle (for example, pedals and a steering wheel).

The processes and methods of the embodiments described in this detailed description and shown in the figures can be implemented using any kind of computing system having one or more central processing units (CPUs) and/or graphics processing units (GPUs). The processes and methods of the embodiments could also be implemented using special purpose circuitry such as an application specific integrated circuit (ASIC). The processes and methods of the embodiments may also be implemented on computing systems including read only memory (ROM) and/or random access memory (RAM), which may be connected to one or more processing units. Examples of computing systems and devices include, but are not limited to: servers, cellular phones, smart phones, tablet computers, notebook computers, e-book readers, laptop or desktop computers, all-in-one computers, as well as various kinds of digital media players.

The processes and methods of the embodiments can be stored as instructions and/or data on non-transitory computer-readable media. The non-transitory computer readable medium may include any suitable computer readable medium, such as a memory, such as RAM, ROM, flash memory, or any other type of memory known in the art. In some embodiments, the non-transitory computer readable medium may include, for example, an electronic storage device, a magnetic storage device, an optical storage device, an electromagnetic storage device, a semiconductor storage device, or any suitable combination of such devices. More specific examples of the non-transitory computer readable medium may include a portable computer diskette, a floppy disk, a hard disk, magnetic disks or tapes, a read-only memory (ROM), a random access memory (RAM), a static random access memory (SRAM), a portable compact disc read-only memory (CD-ROM), an erasable programmable read-only memory (EPROM or Flash memory), electrically erasable programmable read-only memories (EEPROM), a digital versatile disk (DVD and DVD-ROM), a memory stick, other kinds of solid state drives, and any suitable combination of these exemplary media. A non-transitory computer readable medium, as used herein, is not to be construed as being transitory signals, such as radio waves or other freely propagating electromagnetic waves, electromagnetic waves propagating through a waveguide or other transmission media (e.g., light pulses passing through a fiber-optic cable), or electrical signals transmitted through a wire.

Instructions stored on the non-transitory computer readable medium for carrying out operations of the present invention may be instruction-set-architecture (ISA) instructions, assembler instructions, machine instructions, machine dependent instructions, microcode, firmware instructions, configuration data for integrated circuitry, state-setting data, or source code or object code written in any of one or more programming languages, including an object oriented programming language such as Smalltalk, C++, or suitable language, and procedural programming languages, such as the "C" programming language or similar programming languages.

Aspects of the present disclosure are described in association with figures illustrating flowcharts and/or block diagrams of methods, apparatus (systems), and computing products. It will be understood that each block of the flowcharts and/or block diagrams can be implemented by computer readable instructions. The flowcharts and block diagrams in the figures illustrate the architecture, functionality, and operation of possible implementations of various disclosed embodiments. Accordingly, each block in the flowchart or block diagrams may represent a module, segment, or portion of instructions. In some implementations, the functions set forth in the figures and claims may occur in an alternative order than listed and/or illustrated.

The embodiments may utilize any kind of network for communication between separate computing systems. A network can comprise any combination of local area networks (LANs) and/or wide area networks (WANs), using both wired and wireless communication systems. A network may use various known communications technologies and/or protocols. Communication technologies can include, but are not limited to: Ethernet, 802.11, worldwide interoperability for microwave access (WiMAX), mobile broadband (such as CDMA, and LTE), digital subscriber line (DSL), cable internet access, satellite broadband, wireless ISP, fiber optic internet, as well as other wired and wireless technologies. Networking protocols used on a network may include transmission control protocol/Internet protocol (TCP/IP), multiprotocol label switching (MPLS), User Datagram Protocol (UDP), hypertext transport protocol (HTTP), hypertext transport protocol secure (HTTPS) and file transfer protocol (FTP) as well as other protocols.

Data exchanged over a network may be represented using technologies and/or formats including hypertext markup language (HTML), extensible markup language (XML), Atom, JavaScript Object Notation (JSON), YAML, as well as other data exchange formats. In addition, information transferred over a network can be encrypted using conventional encryption technologies such as secure sockets layer (SSL), transport layer security (TLS), and Internet Protocol security (Ipsec).

While various embodiments of the invention have been described, the description is intended to be exemplary, rather than limiting, and it will be apparent to those of ordinary skill in the art that many more embodiments and implementations are possible that are within the scope of the invention. Accordingly, the invention is not to be restricted except in light of the attached claims and their equivalents. Also, various modifications and changes may be made within the scope of the attached claims.

We claim:

1. A motor vehicle, comprising:
 a remote piloting mode, an autonomous driving mode, and a manual driving mode;
 a remote piloting system for operating the motor vehicle in the remote piloting mode;
 an autonomous driving system for operating the motor vehicle in the autonomous driving mode;
 a driver monitoring system, the driver monitoring system configured to detect an unsafe driving condition;
 the driver monitoring system comprising a health monitoring system configured to monitor a health of the driver of the motor vehicle in real time using a health monitoring device worn by the driver;

the driver monitoring system further comprising a behavior monitoring system configured to monitor an outward behavior of the driver of the motor vehicle using one or more sensors associated with the motor vehicle;
wherein the unsafe driving condition is detected based on at least (1) sensed information from the health monitoring device worn by the driver of the motor vehicle, and (2) sensed information from the one or more sensors associated with the motor vehicle;
wherein the motor vehicle automatically switches from the manual driving mode to the remote piloting mode when the unsafe driving condition is detected;
wherein, prior to the unsafe driving condition, the motor vehicle automatically switches from the manual driving mode to one of the remote piloting mode or the autonomous driving mode in response to a voice command from the driver of the motor vehicle;
wherein the remote piloting system is controlled by a family member of the driver who is available and able to remotely control the motor vehicle using a mobile application having virtual controls to remotely operate the motor vehicle; and
when the unsafe driving condition is detected and the driver remains conscious, informing the driver that the motor vehicle has been changed from the manual driving mode to the remote piloting mode.

2. The motor vehicle according to claim 1, wherein the health monitoring device worn by the driver is a smart watch including one or more biometric sensors.

3. The motor vehicle according to claim 1, wherein the one or more sensors associated with the motor vehicle include at least one of a video camera and/or microphone inside the motor vehicle; and
wherein the unsafe driving condition is further detected based on at least sensed information from the at least one of the video camera and/or the microphone.

4. The motor vehicle according to claim 1, wherein the driver monitoring system is configured to receive data from a steering angle sensor.

5. The motor vehicle according to claim 1, wherein the driver monitoring system is configured to receive data from a wheel speed sensor.

6. The motor vehicle according to claim 1, wherein the remote piloting system further comprises a remote piloting interface disposed onboard the motor vehicle, and wherein the remote piloting interface communicates with a remote control system disposed remotely from the motor vehicle operated by the family member of the driver.

7. The motor vehicle according to claim 6, wherein the remote control system is controlled by the family member of the driver located outside of the motor vehicle through the mobile application; and
wherein the remote control system receives sensory information from the one or more sensors associated with the motor vehicle.

8. The method according to claim 1, wherein informing the driver that the motor vehicle has been changed from the manual driving mode to the remote piloting mode includes sending a message to an onboard display in the motor vehicle.

9. The method according to claim 1, wherein informing the driver that the motor vehicle has been changed from the manual driving mode to the remote piloting mode includes making an audible announcement to the driver.

10. A method of controlling a motor vehicle, the motor vehicle being operable in a remote piloting mode, an autonomous driving mode, and a manual driving mode, the method comprising:
monitoring a driver while the motor vehicle is operating in the manual driving mode using a driver monitoring system comprising: (1) a health monitoring system to monitor a health of the driver of the motor vehicle in real time using a health monitoring device worn by the driver, and (2) a behavior monitoring system configured to monitor an outward behavior of the driver of the motor vehicle using one or more sensors associated with the motor vehicle,
wherein monitoring the driver comprises receiving real time health information about the driver from the health monitoring device worn by the driver and receiving sensed information from the one or more sensors associated with the motor vehicle;
detecting an unsafe driving condition from: (1) the real time health information received from the health monitoring device worn by the driver, and (2) the sensed information from the one or more sensors associated with the motor vehicle;
in response to the detected unsafe driving condition, automatically switching the motor vehicle from the manual driving mode to the remote piloting mode;
wherein the motor vehicle includes a remote piloting system for operating the motor vehicle in the remote piloting mode;
wherein the remote piloting system is controlled by a family member of the driver who is available and able to remotely control the motor vehicle using a mobile application having virtual controls to remotely operate the motor vehicle;
when the unsafe driving condition is detected and the driver remains conscious, informing the driver that the motor vehicle has been changed from the manual driving mode to the remote piloting mode;
wherein the motor vehicle further includes an autonomous driving system for operating the motor vehicle in the autonomous driving mode; and
prior to detection of the unsafe driving condition, automatically switching the motor vehicle from the manual driving mode to one of the remote piloting mode or the autonomous driving mode in response to a voice command from the driver of the motor vehicle.

11. The method according to claim 10, wherein the health monitoring device comprises a smart watch including one or more biometric sensors; and
wherein monitoring the driver includes sensing biometric data associated with the driver from the one or more biometric sensors included in the smart watch.

12. The method according to claim 11, wherein the biometric data includes heartrate data.

13. The method according to claim 11, wherein the biometric data includes electrodermal activity.

14. The method according to claim 11, wherein the biometric data includes motion information.

15. The method according to claim 10, wherein the unsafe driving condition is a seizure.

16. The method according to claim 10, wherein informing the driver that the motor vehicle has been changed from the manual driving mode to the remote piloting mode includes sending a message to an onboard display in the motor vehicle.

17. The method according to claim 10, wherein informing the driver that the motor vehicle has been changed from the manual driving mode to the remote piloting mode includes making an audible announcement to the driver.

* * * * *